US011291475B2

(12) United States Patent
Choi et al.

(10) Patent No.: US 11,291,475 B2
(45) Date of Patent: Apr. 5, 2022

(54) TOOL FOR CLOSED REDUCTION OF FRACTURE

(71) Applicants: THE ASAN FOUNDATION, Seoul (KR); UNIVERSITY OF ULSAN FOUNDATION FOR INDUSTRY COOPERATION, Ulsan (KR)

(72) Inventors: Jae Soon Choi, Seoul (KR); Young Jin Moon, Seoul (KR); Jong Woo Choi, Seoul (KR); Ho Yul Lee, Gwangtan-myeon (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 194 days.

(21) Appl. No.: 16/423,943

(22) Filed: May 28, 2019

(65) Prior Publication Data
US 2019/0274732 A1 Sep. 12, 2019

Related U.S. Application Data

(63) Continuation of application No. PCT/KR2017/012980, filed on Nov. 16, 2017.

(30) Foreign Application Priority Data

Nov. 28, 2016 (KR) .................. 10-2016-0159135

(51) Int. Cl.
*A61B 17/56* (2006.01)
*A61B 17/00* (2006.01)
*A61B 17/02* (2006.01)

(52) U.S. Cl.
CPC .............. *A61B 17/56* (2013.01); *A61B 17/00* (2013.01); *A61B 17/00234* (2013.01); *A61B 17/02* (2013.01); *A61B 2017/00792* (2013.01)

(58) Field of Classification Search
CPC ... A61B 17/56; A61B 17/00234; A61B 17/02; A61B 2017/00792
See application file for complete search history.

(56) References Cited

U.S. PATENT DOCUMENTS 4,265,231 A * 5/1981 Scheller, Jr ...... A61B 17/32002
175/61
5,662,683 A * 9/1997 Kay .................. A61B 17/0401
606/232

(Continued)

FOREIGN PATENT DOCUMENTS

CN   2286620 Y    7/1998
CN   2652342 Y    11/2004

(Continued)

OTHER PUBLICATIONS

International Search Report issued in PCT/KR2017/012980; dated Feb. 19, 2018.

(Continued)

*Primary Examiner* — Nicholas J Plionis
(74) *Attorney, Agent, or Firm* — Studebaker & Brackett PC

(57) ABSTRACT

The present disclosure relates to a tool for a closed reduction of a fracture. The tool includes at least: a winding portion having a winding shape; a support extending from the winding portion in a normal direction relative to a plane of the winding shape; and a handle extending from the support in the normal direction, and configured to be gripped.

14 Claims, 22 Drawing Sheets

(56) References Cited

U.S. PATENT DOCUMENTS

| | | | | |
|---|---|---|---|---|
| 8,480,559 | B2* | 7/2013 | Knapp | A61B 50/33 600/37 |
| 2002/0055737 | A1* | 5/2002 | Lieberman | A61B 17/8625 606/247 |
| 2004/0133217 | A1* | 7/2004 | Watschke | A61B 17/06109 606/148 |
| 2011/0106186 | A1 | 5/2011 | Wolfson | |
| 2011/0166660 | A1* | 7/2011 | Laurence | A61F 2/4455 623/17.16 |
| 2011/0190764 | A1* | 8/2011 | Long | A61B 18/1477 606/41 |

FOREIGN PATENT DOCUMENTS

| | | |
|---|---|---|
| GB | 1281863 A | 7/1972 |
| KR | 10-0536168 B1 | 12/2005 |

OTHER PUBLICATIONS

Surginstruments; Doyen Rib Elevator Curved 7" Right Surgical Instruments; ebay.com; Dec. 4, 2013.
Office Action issued in KR 10-2016-0159135; mailed by the Korean Intellectual Property Office dated Jan. 9, 2018.
Cardiovascular Surgical Instruments Published : http://elitelifecare.com/?page_id=2515, [www.archive.org] (Aug. 8, 2016).
Cardiovascular Surgical Instruments detailed drawings : http://elitelifecase.com/?page_id=2515, [www.archive.org].
An Office Action mailed by the Korean Intellectual Property Office dated Jun. 12, 2019, which corresponds to Korean Patent Application No. 10-2019-0026965 and is related to U.S. Appl. No. 16/423,943.
The extended European search report issued by the European Patent Office dated Nov. 20, 2019, which corresponds to European Patent Application No. 17874299.5-1122 and is related to U.S. Appl. No. 16/423,943.

* cited by examiner

TOOL FOR CLOSED REDUCTION OF FRACTURE

CROSS-REFERENCE TO RELATED APPLICATIONS

The present application is a continuation of International Patent Application No. PCT/KR2017/012980, filed Nov. 16, 2017, which is based upon and claims the benefit of priority to Korean Patent Application No. 10-2016-0159135, filed on Nov. 28, 2016. The disclosures of the above-listed applications are hereby incorporated by reference herein in their entirety.

BACKGROUND

Embodiments of the present invention described herein relate to a closed reduction tool for a bone fracture, and more particularly to a closed reduction tool for a bone fracture to restore depressed bone fragments.

Generally, a plastic surgery is being performed for patients having depressed bone fragments in a facial region due to an external impact.

Such a surgical operation is performed by inserting a rigid surgical instrument into a region having the depressed fragments optionally by incision thereof, and unfolding or lifting the depressed bone fragments using a principle of lever.

For example, when the rigid instrument is inserted into between the depressed bone fragments in which in turn are lifted by the instrument, this lifting operation may damage other bones surrounding the region having the depressed fragments.

Further, there is a problem that when a direction of a force for lifting the bone out is different from a transmission direction of a force from the surgical instrument, that is, both directions of the forces non-coincide with each other, it is difficult to smoothly transmit the lifting force to the damaged bond fragments via the instrument.

Accordingly, since other bones may be damaged during the surgical procedure, in many cases, a skin is incised to perform a further operation to restore the damaged bone fragments.

Although a need for a surgical instrument for minimally invasive surgery to minimize scar is increasing, development of such a surgical instrument has not been accomplished as expected.

When a conventional surgical instrument is used, for example, for treatment of a frontal sinus fracture having many bone fragments, a bone fragment at one side of the leverage is reduced (restored), while a bone fragment at the other side of the leverage area is more dislocated.

For this reason, there occurs a need for developing a surgical instrument capable of being inserted into a small incision window, and of vertically lifting a bone fragment at one side thereof while not applying force to a bone fragment at the other side thereof, or of lifting a plurality of bone fragments at the same time.

SUMMARY

Embodiments of the present invention are to solve the above-mentioned problem and is to provide a closed reduction tool for a bone fracture that can be easily inserted and removed through a small incision window and can lift a depressed fractured piece stably to restore the same.

Further, embodiments of the present invention are to provide a closed reduction tool for a bone fracture which may be supported on various portions and may change a direction of lifting thereof, and may restoring a fractured piece stably via minimization of fluctuation of a handle and a spiral portion thereof when an operator lifts the fractured piece.

Further, embodiments of the present invention are to provide a closed reduction tool for a bone fracture which may finely tune and lift a depressed bone fragments to restore the bone fragments.

According to an exemplary embodiment, a closed reduction tool for a bone fracture includes at least: a winding portion having a winding shape; a support extending from the winding portion in a normal direction relative to a plane of the winding shape; and a handle extending from the support in the normal direction, and configured to be gripped, wherein the winding portion is configured to be inserted into between depressed bone fragments and lift the depressed bone fragments.

BRIEF DESCRIPTION OF DRAWINGS

The above and other objects and features will become apparent from the following description with reference to the following figures, wherein like reference numerals refer to like parts throughout the various figures unless otherwise specified, and wherein.

DETAILED DESCRIPTION

Figure 1:
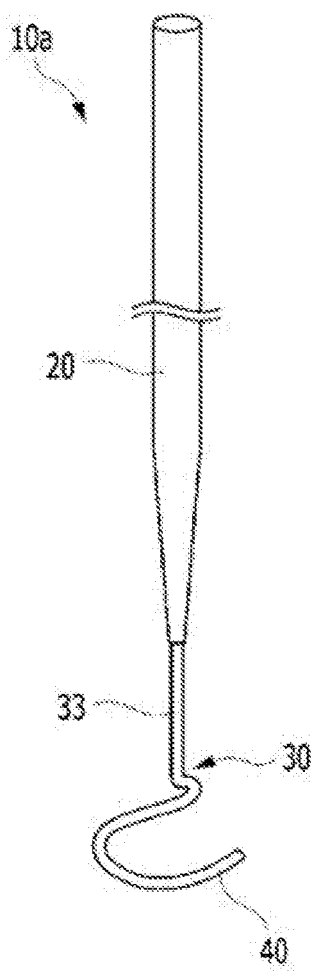
FIG. 1 is a perspective view of a closed reduction tool for a bone fracture according to some embodiments of the present disclosure.

Hereinafter, preferred embodiments of the present invention will be described in detail with reference to the accompanying drawings. Advantages and features of the present invention, and methods of accomplishing the same, will become apparent with reference to the embodiments described in detail below with reference to the accompanying drawings. However, the present invention is not limited to the embodiments disclosed below, but may be embodied in various forms. These embodiments are provided so that the disclosure of the present invention is complete and that it is believed that the disclosure is intended to be completely understood by those skilled in the art to which the present invention belongs.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Unless otherwise defined, all terms including technical and scientific terms used herein have the same meaning as commonly understood by one of ordinary skill in the art to which this present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention will now be described in detail with reference to the accompanying drawings.

Prior to the description, followings should be noted: components having the same configuration between various embodiments may be denoted by the same reference numeral; the component having the same configuration will be first described with reference to the first embodiment, and description thereof will be omitted in remaining embodiments; only components as disclosed in the first embodiment will be described in the remaining embodiments.

Further, the closed reduction tool for a bone fracture according to the present invention may be applied not only to a facial bone but also to various bone portions of the human body.

Figure 2:
FIG. 2 is a front view of the closed reduction tool shown in FIG. 1.

FIG. 1 and FIG. 2 show a closed reduction tool for a bone fracture according to a first embodiment of the present disclosure.

As shown in FIGS. 1 and 2, a closed reduction tool 10a according to the first embodiment includes a handle 20, a support 30, and a winding portion 40.

The handle 20 has a cylindrical shape on which an operator is capable of gripping the tool 10a. An end portion of the handle 20 facing the support 30 has a tapered shape. In some embodiments, the handle 20 has a projection on a surface thereof or has an anti-slip pad made of rubber thereon, to prevent the handle from slipping on the hand of the operator when the operator is inserting or lifting the closed reduction tool 10a.

The support 30 has a wire shape having a predetermined length, and extends along a central axis of the handle 20 and from an end of the handle 20.

In some embodiments, the support 30 has a straight portion 33 and a distal end. The distal end of the support 30 is helically extending from the straight portion 33 and around the central axis of the handle 20 by a helical radius larger than a radius of the handle 20, thereby to configure a step between the straight portion 33 and the winding portion 40. The distal end of the support 30 connects to the winding portion 40. Thus, the distal end of the support 30 configures a step between the straight portion 33 of the support 30 and the winding portion 40.

The winding portion 40 has a wire shape and has a winding shape. In some embodiments, the winding shape is a spiral shape, and in some embodiments, the winding shape is a half-spiral shape. The winding portion 40 extends from the support 30, and the support 30 extends from the winding portion 40 in a normal direction relative to a plane of the winding shape. In some embodiments, the winding portion 40 has a left-oriented winding shape with a radius greater than the radius of the handle 20. In some embodiments, the winding portion 40 is wound in a coplanar manner and has a flat shape.

The closed reduction tool 10a according to the first embodiment is configured to be inserted into an incision window 3 (shown in FIGS. 15A to 15C) between depressed bone fragments 1 (shown in FIGS. 15A to 15C) in an inclined manner. The closed reduction tool 10a according to the first embodiment is useful when there is a sufficient space inside the depressed bone fragments 1. The closed reduction tool 10a according to the first embodiment is embodied as a closed reduction tool for a bone fracture with a relatively large helical radius and has a large contact area with the bone after being inserted inside the bone.

Figure 3:
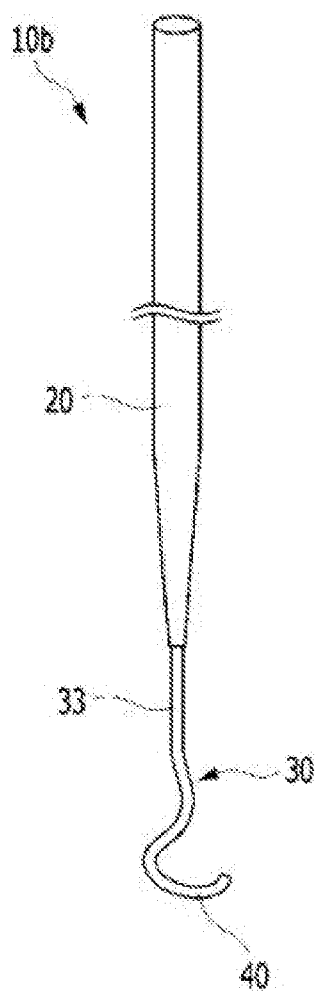
FIG. 3 is a perspective view of a closed reduction tool for a bone fracture according to some embodiments of the present disclosure.
Figure 4:
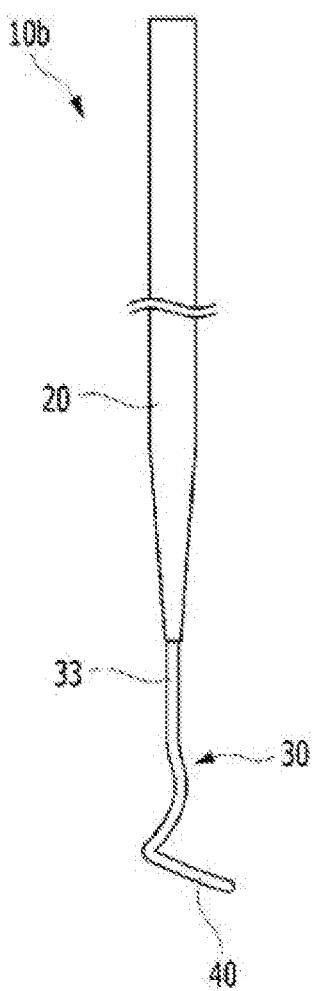
FIG. 4 is a front view of the closed reduction tool shown in FIG. 3.

FIG. 3 and FIG. 4 show a closed reduction tool for a bone fracture according to a second embodiment of the present disclosure.

As shown in FIGS. 3 and 4, a closed reduction tool 10b according to the second embodiment differs from that the closed reduction tool 10a of the first embodiment described above in that the winding portion 40 extends in a non-coplanar manner, and extends from the support 30 in a half-spiral shape around the central axis of the handle 20. Further, in the second embodiment, the winding portion 40 extends in an inclined manner with respect to the central axis of the handle 20, and the winding portion 40 is wound with a helical radius smaller than that of the winding portion 40 of the first embodiment.

The closed reduction tool 10b according to the second embodiment is configured to be inserted into the incision window 3 (shown in FIGS. 15A to 15C) between depressed bone fragments 1 (shown in FIGS. 15A to 15C) in an erected manner. The closed reduction tool 10b according to the second embodiment is useful when there is an in sufficient space inside the depressed bone fragments 1.

Figure 5:
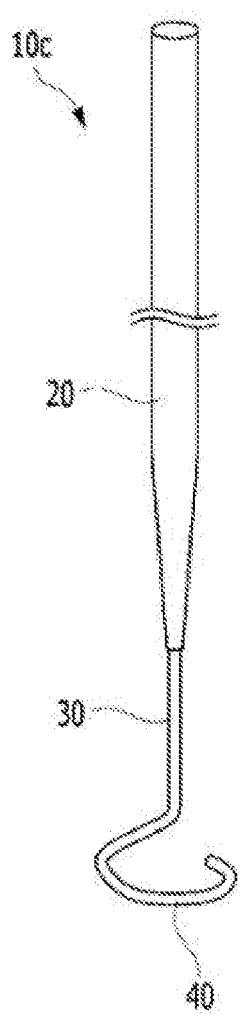
FIG. 5 is a perspective view of a closed reduction tool for a bone fracture according to some embodiments of the present disclosure.
Figure 6:
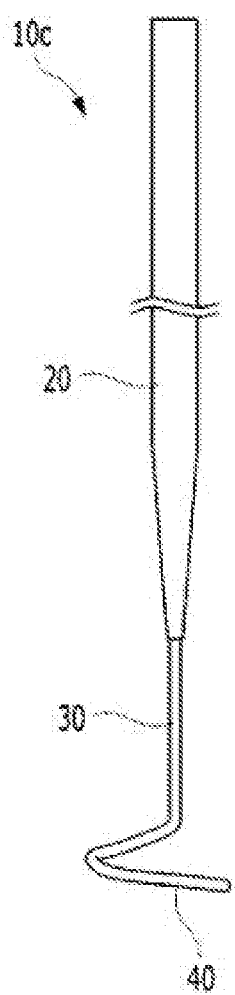
FIG. 6 is a front view of the closed reduction tool shown in FIG. 5.

FIG. 5 and FIG. 6 show a closed reduction tool for a bone fracture according to a third embodiment of the present disclosure.

As shown in FIGS. 5 and 6, a closed reduction tool 10c according to the third embodiment differs from the closed reduction tool 10a of the first embodiment described above in that the winding portion 40 extends in a non-coplanar manner, and differs from the closed reduction tool 10b of the second embodiment described above in that the distal end of the support 30 extends in a straight manner. The winding portion 40 of the closed reduction tool 10c extends in a half-spiral shape around the central axis of the handle 20.

Figure 15A:
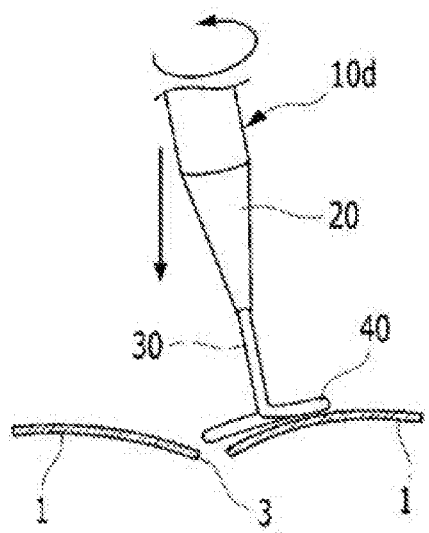
FIGS. 15A to 15C are views illustrating a procedure of operation using a closed reduction tool for a bone fracture according to some embodiments of the present disclosure.
Figure 15B:
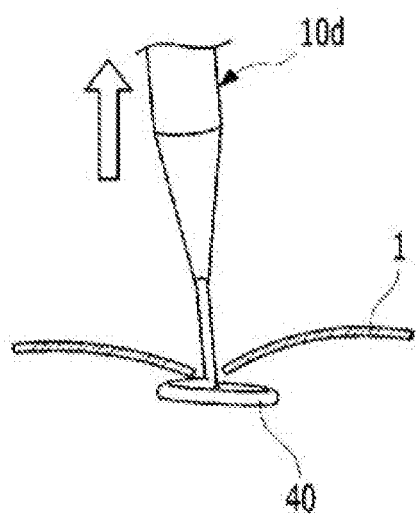
Figure 15C:
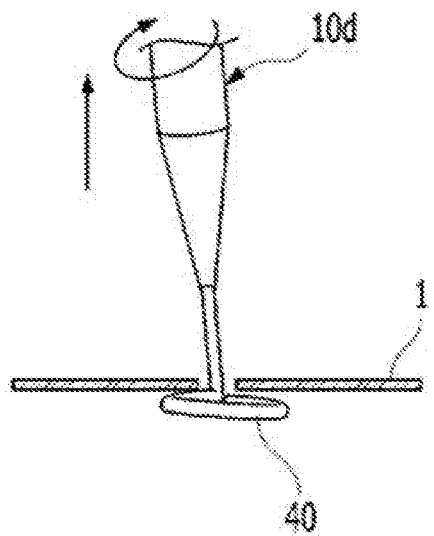

The closed reduction tool 10c according to the third embodiment is useful when a wide tool cannot be inserted into between the bone fragments due to a thickness and a size of the depressed bone fragments 1 (shown in FIGS. 15A to 15C). Further, the closed reduction tool 10c according to the third embodiment is configured to be inserted into between the bone fragments 1 and to be lifted while rotating the closed reduction tool 10c.

Figure 7:
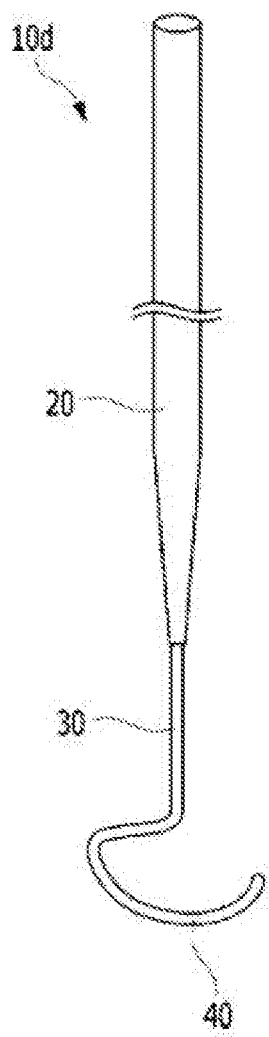
FIG. 7 is a perspective view of a closed reduction tool for a bone fracture according to some embodiments of the present disclosure.
Figure 8:
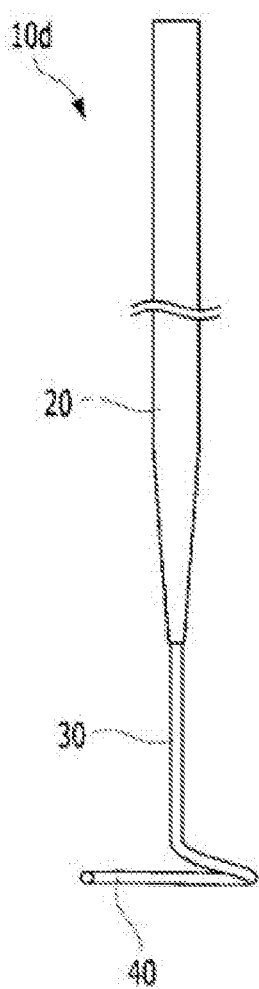
FIG. 8 is a front view of the closed reduction tool shown in FIG. 7.

FIG. 7 and FIG. 8 show a closed reduction tool for a bone fracture according to a fourth embodiment of the present disclosure.

As shown in FIGS. 7 and 8, a closed reduction tool 10d according to the fourth embodiment differs from the closed reduction tool 10a of the first embodiment described above in that the distal end of the support 30 extends in a straight manner. The winding portion 40 of the closed reduction tool 10d extends in a coplanar manner. The winding portion 40 of the closed reduction tool 10d extends in a half-spiral shape around the central axis of the handle 20. Further, a plane defined by the winding portion 40 is perpendicular to the central axis of the handle 20.

As a result, the closed reduction tool 10d according to the fourth embodiment has no step between the support 30 and the winding portion 40.

The closed reduction tool 10d according to the fourth embodiment is constructed such that a contact face between the depressed bone fragments 1 and the winding portion 40 is at a right angle with a lifting axis, thereby to easily lift the depressed bone fragments 1.

Figure 9:
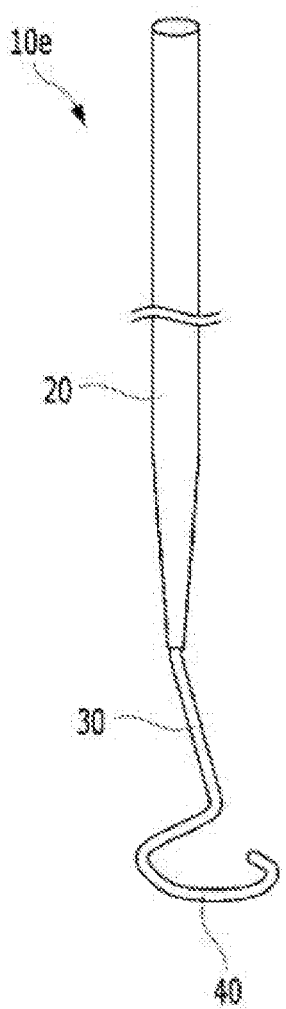
FIG. 9 is a perspective view of a closed reduction tool for a bone fracture some embodiments of the present disclosure.
Figure 10:
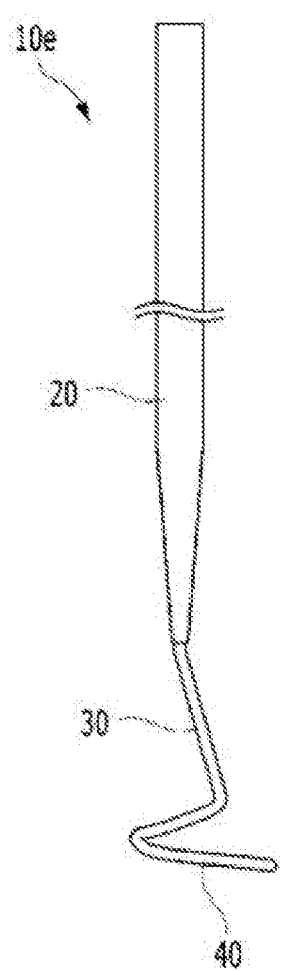
FIG. 10 is a front view of the closed reduction tool shown in FIG. 9.
Figure 11:
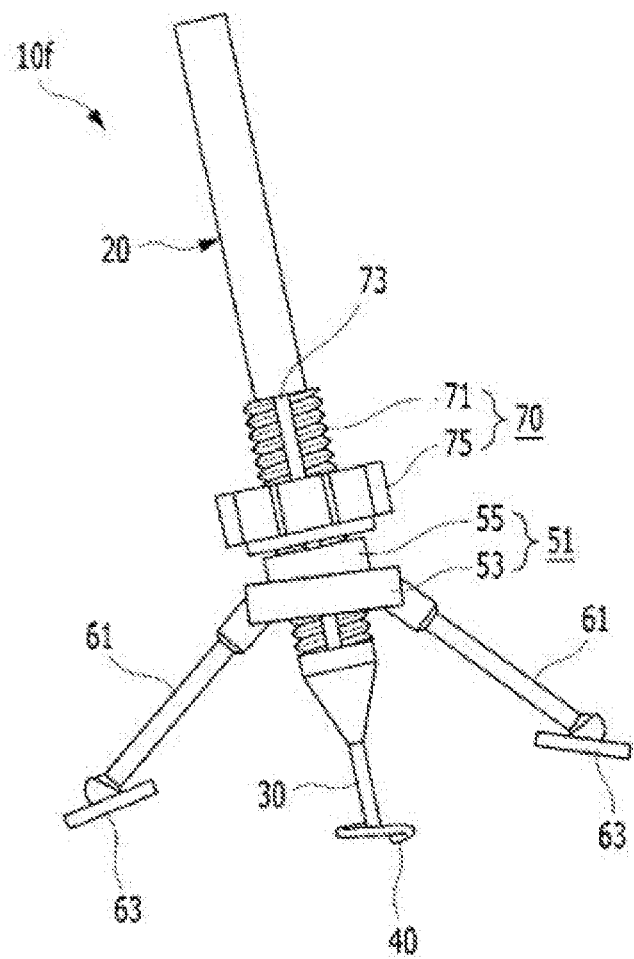
FIG. 11 is a perspective view of a closed reduction tool for a bone fracture according to some embodiments of the present disclosure.
Figure 12:
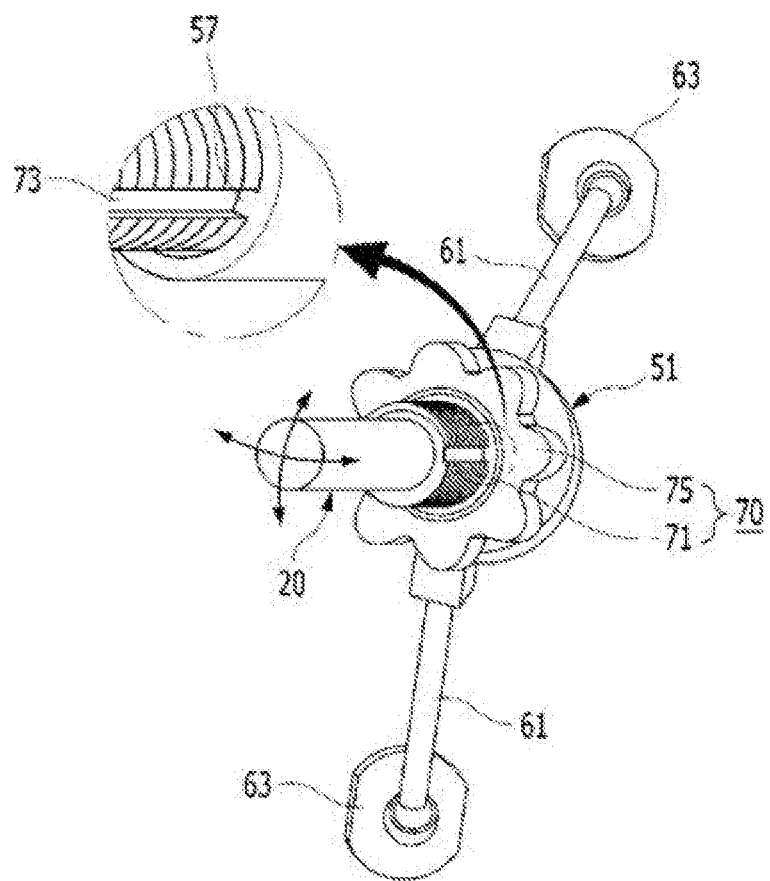
FIG. 12 is a top perspective view of the closed reduction tool shown in FIG. 11.
Figure 13:
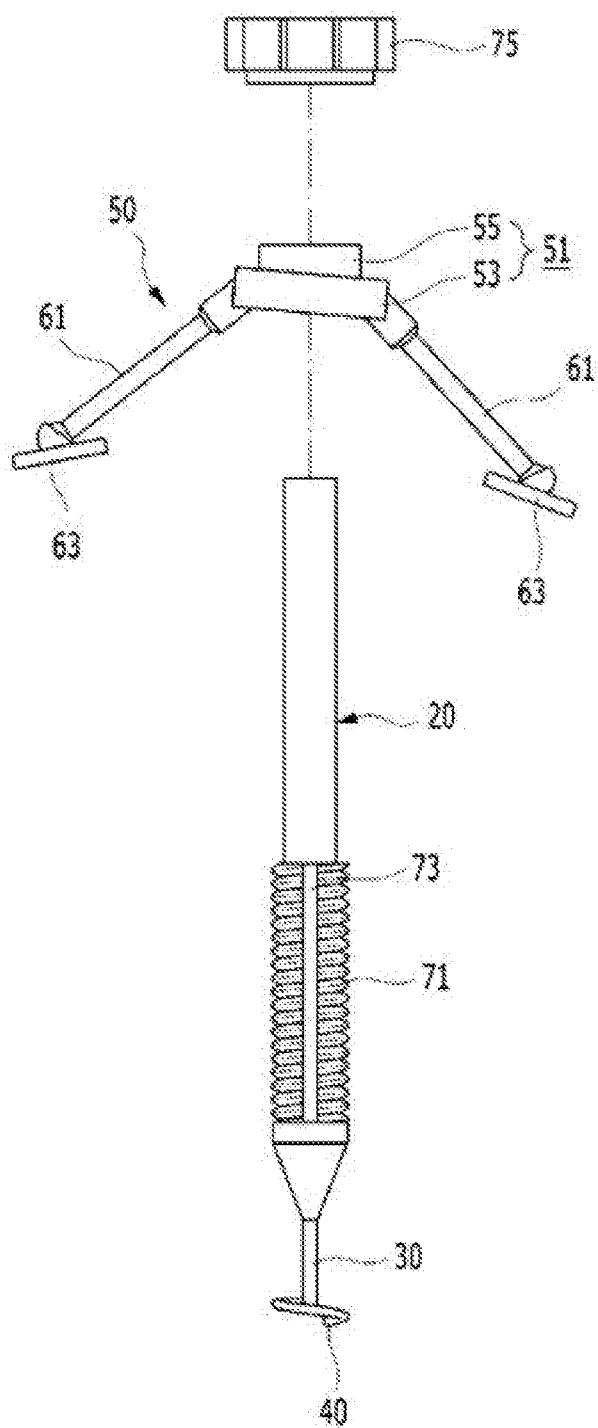
FIG. 13 is an exploded perspective view of the closed reduction tool shown in FIG. 11.

FIG. 9 and FIG. 10 show a closed reduction tool for a bone fracture according to a fifth embodiment of the present disclosure.

As shown in FIGS. 9 and 10, a closed reduction tool 10e according to the fifth embodiment differs from the closed reduction tool 10c of the third embodiment as described above in that the support 30 extends in an inclined with respect to the central axis of the handle 20.

The closed reduction tool 10e according to the fifth embodiment is useful when the tool 10e is required to be inclined obliquely to be inserted through the incision window 3 between the depressed bone fragments 1.

Although the winding portion 40 of each of the first to fifth embodiments as described above is shown as being formed in a left-oriented winding shape, the present disclosure is not limited thereto. In some embodiments, the winding portion 40 is formed in a right-oriented winding shape.

One of the closed reduction tools according to the first to fifth embodiments having various winding portions 40 according to the above defined configuration may be selected based on a size and position of the bone fragments 1 and then may be inserted through the incision window 3 between the bone fragments 1. Then, the operator is able to lift the bone fragments 1 concurrently to perform the reduction operation of the bone.

FIGS. 15A to 15C are diagrams illustrating a procedure for performing bone reduction surgery using the closed reduction tool 10d according to the fourth embodiment by way of example.

Referring briefly to the procedure of the operation with reference to FIGS. 15A to 15C, as shown in FIG. 15A, an operator places the closed reduction tool 10d according to the fourth embodiment in the erected manner onto the incision window 3 between the bone fragments 1. Then, the operator grips the handle 20 and rotates the winding portion 40 in one direction and inserts the winding portion 40 into between the bone fragments 1 through the incision window 3.

Then, as shown in FIG. 15B, the operator lifts the depressed bone fragments 1 while a wide contact face between the winding portion 40 and bone fragments 1 is maintained. In this connection, the closed reduction tool 10d according to the fourth embodiment lifts the depressed bone fragments 1 in the vertical direction, differently from the conventional manner, such that damage to other surrounding bones is prevented.

Then, when the bone fragments 1 is reduced or recovered, as shown in FIG. 15C, the operator lifts the closed reduction tool 10d according to the fourth embodiment from the bone fragments 1 while the operator rotates the winding portion 40 in an direction opposite to the direction for insertion. This completes the reduction of the bone fragments 1.

In this regard, when the incision window 3 is not formed between the bone fragments 1, the operator may form the incision window 3 between the bone fragments 1 using a drill (not shown). Then, the operator may perform a reduction operation by inserting the closed reduction tool for the bone fracture having a diameter corresponding to a diameter of the incision window 3 through the incision window 3 and lifting the bone fragments 1.

FIGS. 16A to 16E are diagrams illustrating an alternative operation procedure using the closed reduction tool 10d according to the fourth embodiment.

Figure 16A:
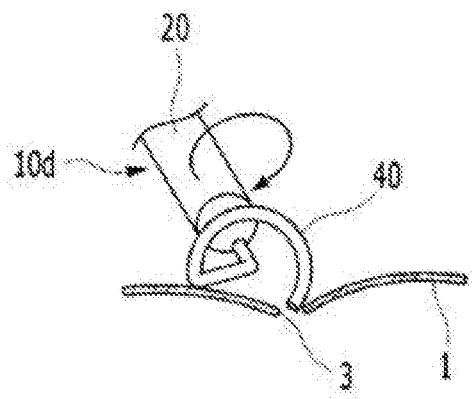
FIGS. 16A to 16E are views illustrating a procedure of another operation using a closed reduction tool for a bone fracture according to some embodiments of the present disclosure.
Figure 16B:
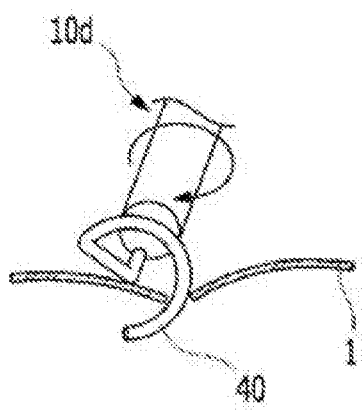

Referring briefly to the procedure of the operation with reference to FIGS. 16A to 16E, as shown in FIG. 16A, the operator tilts the closed reduction tool 10d according to the fourth embodiment with respect to the incision window 3 between the bone fragments 1. Then, as shown in FIG. 16B, the operator grasps the handle 20 of the closed reduction tool 10d, rotates the winding portion 40 thereof in one direction to insert the winding portion 40 through the incision window 3 into between the bone fragments 1.

Figure 16C:
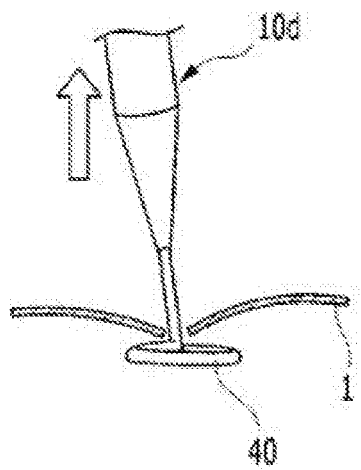

Then, as shown in FIG. 16C, in a state where the winding portion 40 of the closed reduction tool 10d is inserted into between the bone fragments 1, the operator orients the closed reduction tool 10d in a perpendicular direction to the incision window 3 between the bone fragments 1. Then, the operator lifts the depressed bone fragments 1 while the wide contact surface between the winding portion 40 and the depressed bone fragments 1 is maintained. In this connection, the depressed bone fragments 1 are lifted in the vertical direction to prevent the damage to other surrounding bones.

Figure 16D:
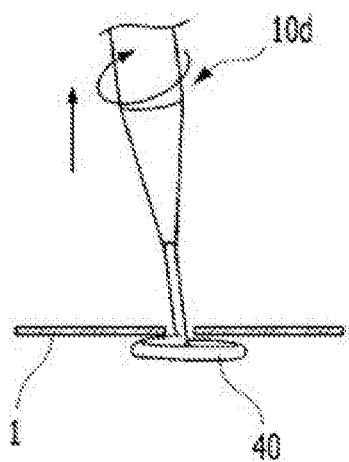
Figure 16E:
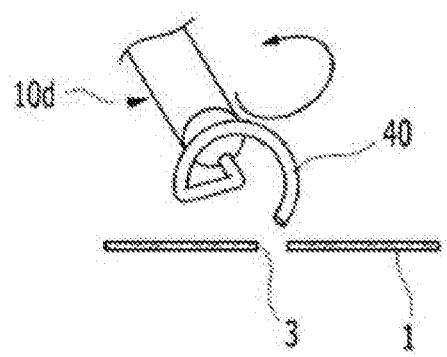

Then, when the bone fragments 1 are reduced or recovered, the operator rotates the winding portion 40 in an opposite direction to the direction for insertion, as shown in FIG. 16D. As shown in FIG. 16E, the operator tilts the closed reduction tool 10d with respect to the incision window 3 between the bone fragments 1 in the same manner as in the insertion of the closed reduction tool 10d. In this state, the operator lifts the closed reduction tool 10d out of the bone fragments 1 while rotating the winding portion 40 in an opposite direction to the direction for the insertion. In this way, the reduction of the bone fragments 1 is completed.

FIGS. 11 to 14 show a closed reduction tool for a bone fracture according to a sixth embodiment of the present disclosure.

A closed reduction tool 10f according to the sixth embodiment further includes a fixture 50, unlike the first to fifth embodiments described above.

The fixture 50 includes a pivot joint 51 and a plurality of pivotable legs 61.

Figure 14:
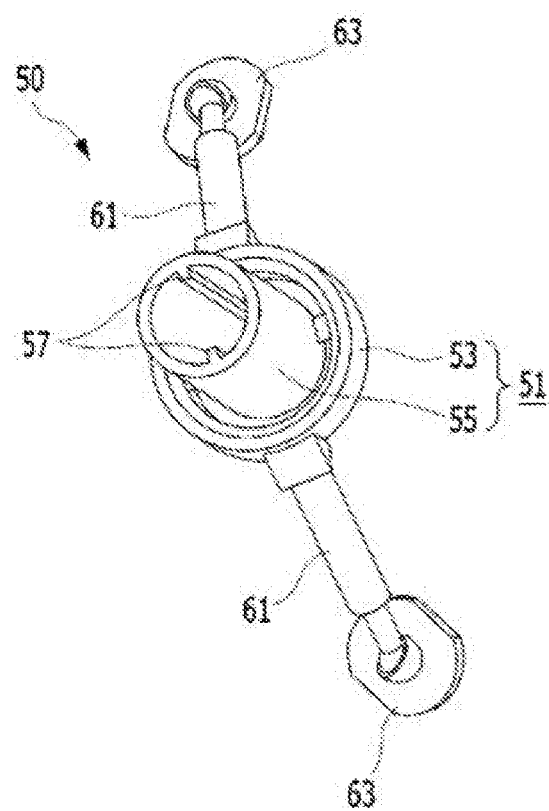
FIG. 14 is a perspective view of the pivot joint shown in FIG. 11.

The pivot joint 51 includes a joint body 53 and a sleeve 55 pivotally coupled to the joint body 53, as shown in FIG. 14.

The sleeve 55 has a hollow pipe shape with a circular cross section, and the handle 20 is pivotally supported on the sleeve 55 so as to be linearly movable. Further, a pair of guide protrusions 57 are formed on an inner circumference of the sleeve 55. The pair of guide protrusions 57 protrude to a predetermined height along an inserting direction of the handle 20, for example, in a longitudinal direction of the sleeve 55. The pair of guide protrusions 57 are positioned symmetrically on the inner circumference of the sleeve 55.

The plurality of pivotable legs 61 are provided on an outer surface of the pivot joint 51 to support the pivot joint 51 to be spaced from the bone fragments 1.

Further, the plurality of pivotable legs 61 are pivotally hinged to the pivot joint 51. As a result, the fixture is stably mounted on a portion to be operated having a straight shape, or on various portions having concaved or convex curved shapes.

A pad 63, which is resiliently supported around the bone fragments 1, is mounted on at each distal end of each of the pivotable legs 61. In some embodiments, the pad 63 is made of rubber or silicon material.

Further, the closed reduction tool 10e according to the sixth embodiment further includes a lifter 70 for lifting the handle 20 pivotally supported on the fixture 50.

In some embodiments, the lifter 70 includes a threaded portion 71 and a knob 75.

In some embodiments, the threaded portion 71 is positioned on a portion of an outer circumferential surface of the handle 20. That is, in some embodiments, the threaded portion 71 is positioned on the portion of the outer circumferential surface of the handle 20 passing through the pivot joint 51. The threaded portion 71 has a pair of guide grooves 73 depressed to a predetermined depth along the longitudinal direction of the handle 20 in correspondence with the pair of guide protrusions 57 of the pivot joint 51. Each of the guide protrusions 57 of the pivot joint 51 is movably fitted in each of the guide grooves 73 of the handle 20.

The knob 75 is screw-coupled to the threaded portion 71 to be sliding on the pivot joint 51. In some embodiments, a thread of the same size as that of the thread of the threaded portion 71 is formed on an inner circumference of the knob 75. According to these features, in some embodiments, the knob 75 vertically moves the handle 20 toward or away from the bone fragments 1 via screw movement between the knob 75 and the threaded portion 71.

That is, when the knob 75 is rotated in one direction while the knob 75 is sliding on the pivot joint 51, the handle 20 having the threaded portion 71 is raised. Conversely, when the knob 75 is rotated in an opposite direction while the knob 75 is sliding on the pivot joint 51, the handle 20 having the threaded portion 71 is lowered.

When an operator rotates the knob 75 in one direction or the opposite direction while sliding the knob 75 on the pivot joint 51, the handle 20 does not rotate with respect to the pivot joint 51, but stably and linearly moves up and down because each guide protrusion 57 of the pivot joint 51 is movably fitted into each guide groove 73 of the handle 20.

Figure 17:
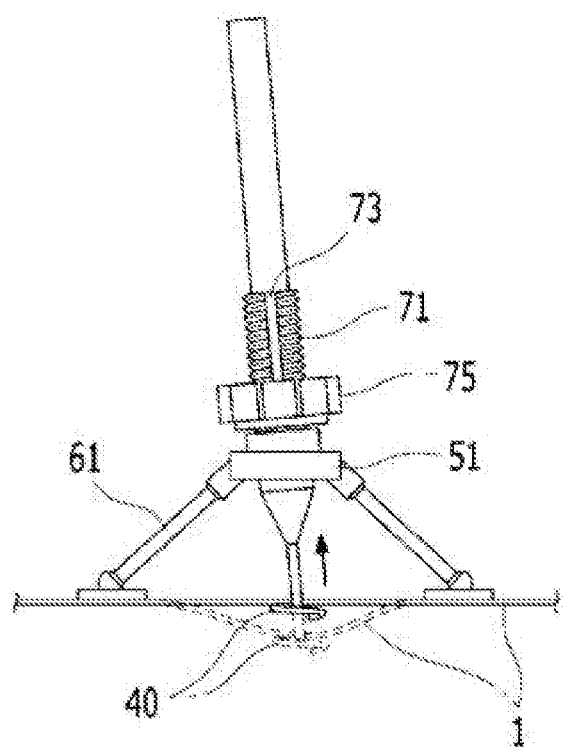
FIG. 17 is a view showing a state in which a closed reduction tool for a bone fracture according to some embodiments of the present disclosure is mounted on a straight shaped fractured piece.

FIG. 17 shows a state in which the closed reduction tool 10e according to the sixth embodiment is mounted on a straight shaped fractured piece.

Figure 18:
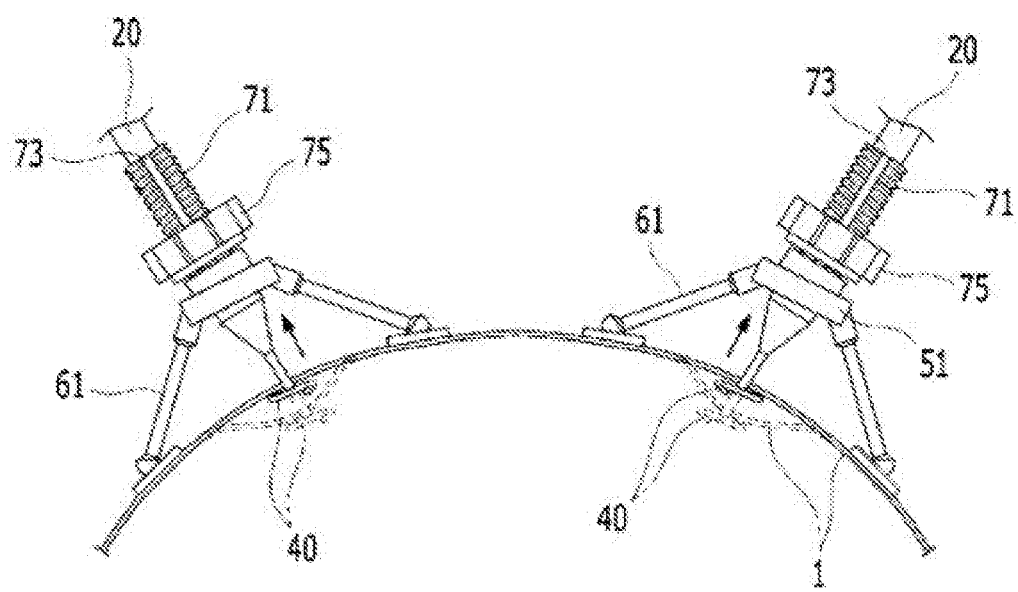
FIG. 18 is a view showing a state in which a closed reduction tool for a bone fracture according to some embodiments of the present disclosure is mounted on a fractured piece having a curved shape.

Further, FIG. 18 shows a state in which the closed reduction tool 10e to the sixth embodiment is mounted on a fractured piece having a curved shape.

Figure 19:
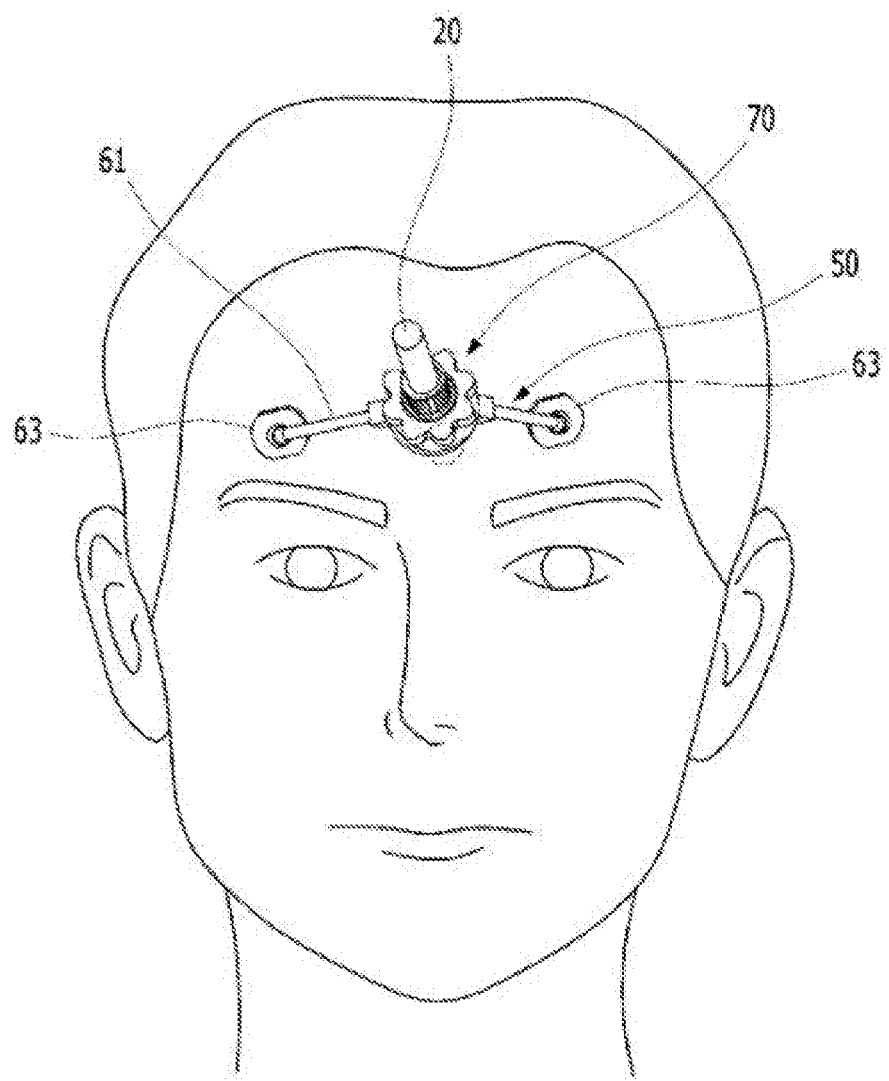
FIG. 19 is a view showing a state in which a closed reduction tool for a bone fracture according to some embodiments of the present disclosure is mounted on a face.

Furthermore, FIG. 19 is a view showing a state in which the closed reduction tool 10e according to the sixth embodiment is mounted on a face of a subject.

Using the above configurations, the winding portion 40 of the closed reduction tool 10e according to the sixth embodiment is inserted through the incision window 3 between the bone fragments 1. Then, the handle 20 is mounted on the fixture 50 so as to penetrate the pivot joint 51. In this connection, an operator places each pivotable leg 61 of the fixture 50 around the bone fragments 1.

While the handle 20 is supported on the pivot joint 51, the operator screws the knob 75 to the threaded portion 71 of the handle 20.

Then, the operator rotates the knob 75 in one direction while sliding the knob 75 on the pivot joint 51, the handle 20 with the threaded portion 71 is raised up from the bone fragments 1.

As the knob 75 rotates, the handle 20 rises up, for example, the winding portion 40 rises up, thereby to lift the depressed bone fragments 1 while the wide contact surface between the depressed bone fragments 1 and the winding portion 40 is maintained.

In this connection, the handle 20 is stably supported by the fixture 50. Thus, when the operator lifts the bone fragments 1, vibrations of the handle 20 and the winding portion 40 are minimized. Thus, the bone fragments 1 can be stably reduced or recovered. Further, as an upward movement of the winding portion 40 by the lifter 70 is finely tuned, the depressed bone fragments 1 are precisely tuned and lifted for the recovery.

In this connection, the closed reduction tool 10e according to the sixth embodiment may be used without the lifter 70. That is, after the operator holds the handle 20 and inserts the winding portion 40 through the incision window 3 between the bone fragments 1, the operator mounts the fixture 50 so that the handle 20 passes through the pivot joint 51. In this connection, each pivotable leg 61 of the fixture 50 is placed around the bone fragments 1.

While the handle 20 is supported on the pivot joint 51, the operator lifts the handle 20 to be spaced from the bone fragments 1 while the wide contact surface between the winding portion 40 and the depressed bone fragments 1 is maintained. In this connection, the handle 20 is stably fixed by the fixture 50. Thus, the tool may be mounted on various body portions and the lifting direction of the handle may vary. When the operator lifts the bone fragments 1, fluctuations of the handle 20 and the winding portion 40 are minimized, so that the bone fragments 1 are stably reduced or recovered.

According to the present disclosure, the tool has the winding portion of a helical shape that is configured to be inserted into a small incision window between depressed bone fragments, and thus simultaneously lift the bone fragments. That is, the tool may be easily inserted and be removed through the small incision window and may reliably restore the depressed bone fragments by lifting the depressed bone fragments.

Further, the handle is held on the fixture and is lifted. Thus, the tool may be supported on various body portions and a direction of lifting the tool may be changed. Further, when the operator lifts the bone fragments, the fluctuation of the handle and the winding portion is minimized, thereby to reduce the bone fragments reliably.

Moreover, providing the lifter that lifts the handle pivotably held by the fixture allows the depressed bone fragments to be precisely tuned and lifted by the operator and to be reliably reduced.

While the present disclosure has been described with reference to exemplary embodiments, it will be apparent to those skilled in the art that various changes and modifications may be made without departing from the spirit and scope of the present invention. Therefore, it should be understood that the above embodiments are not limiting, but illustrative.

What is claimed is:

1. A closed reduction tool for a bone fracture, the tool comprising:
    a winding portion having a winding shape;
    a support extending from the winding portion in a normal direction relative to a plane of the winding shape;
    a handle extending from the support in the normal direction, and configured to be gripped,
    wherein the winding portion is configured to be inserted between depressed bone fragments and lift the depressed bone fragments; and
    a fixture that comprises:
        a pivot joint configured to pivotally support the handle so as to allow a linear movement of the handle; and
        a plurality of pivotable legs coupled to the pivot joint, and configured to support the pivot joint to be spaced from the depressed bone fragments.

2. The closed reduction tool of claim 1, further comprising:
    a lifter configured to lift the handle that is pivotally supported on the fixture.

3. The closed reduction tool of claim 2, wherein the lifter comprises:
    a threaded portion positioned on a portion of a circumferential surface of the handle; and
    a knob screw-coupled to the threaded portion, and configured to be sliding on the pivot joint,
    wherein a screw-movement between the knob and the threaded portion allows the handle to be spaced from the depressed bone fragments.

4. The closed reduction tool of claim 3, further comprising:
    a guide groove positioned in the threaded portion, having a predetermined depth, and extending along a longitudinal direction of the handle; and
    a guide protrusion protruding from the pivot joint, having a predetermined height, and being movably coupled with the guide groove.

5. The closed reduction tool of claim 1, wherein the plurality of pivotable legs are pivotally coupled to the pivot joint.

6. The closed reduction tool of claim 1, further comprising:
    pads each of which is mounted on a respective distal end of a respective pivotable leg, configured to elastically support the respective pivotable leg and be positioned around the depressed bone fragments.

7. The closed reduction tool of claim 1, wherein a winding radius of the winding portion is greater than a radius of the handle.

8. The closed reduction tool of claim DOM, wherein the winding portion is wound in a coplanar manner.

9. The closed reduction tool of claim 1, wherein the support comprises a straight portion and a distal end, wherein the distal end has a winding shape.

10. The closed reduction tool of claim 1, wherein a distal end of the support is windingly extended around a central axis of the handle so as to configure a step between the support and the winding portion, wherein the distal end is connected to the winding portion.

11. The closed reduction tool of claim 1, wherein the winding portion is wound into a direction perpendicular to a central axis of the handle.

12. The closed reduction tool of claim 1, wherein the winding portion has a spiral shape.

13. The closed reduction tool of claim 1, wherein the winding portion has a half-spiral shape.

14. The closed reduction tool of claim 1, wherein the support extends in an inclined manner with respect to a central axis of the handle.

* * * * *